United States Patent [19]
Hinokuma et al.

[11] Patent Number: 5,869,723
[45] Date of Patent: Feb. 9, 1999

[54] IONIC COMPOUND AND OLEFIN POLYMERIZATION CATALYST CONTAINING THE SAME

[75] Inventors: Shinji Hinokuma; Shigenobu Miyake; Michio Ono; Shintaro Inazawa, all of Oita, Japan

[73] Assignee: Showa Denko K.K., Tokyo, Japan

[21] Appl. No.: 776,777

[22] PCT Filed: Jun. 5, 1996

[86] PCT No.: PCT/JP96/01514

§ 371 Date: Feb. 10, 1997

§ 102(e) Date: Feb. 10, 1997

[87] PCT Pub. No.: WO96/41808

PCT Pub. Date: Dec. 27, 1996

[30] Foreign Application Priority Data

Jun. 8, 1995 [JP] Japan .................................. 7-142145

[51] Int. Cl.$^6$ ......................................................... C07F 7/02
[52] U.S. Cl. ................... 556/402; 568/1; 568/6; 556/173; 556/9; 502/158; 502/203; 502/231
[58] Field of Search ................................ 568/1, 6; 556/9, 556/173, 402; 502/152, 158, 203, 231

[56] References Cited

PUBLICATIONS

CA:106:18652 abs of J Am Chem Soc, by Katz, 108(24) pp. 7640–7645, 1986.
Cas registry No. 186499–67–2, Feb. 1997.
CA:96:52379, abs of "Synthesis and Reactivity of trimethylsilylboranes", Liebigs Ann Chem, Werner, (11), pp. 2067–2080, 1981.
CA:95:497897, abs of "Simple nucleophilic silylation reaction on carbonyl functions with trimethylsilylaluminum compounds". Agnew Chem, Lutz, 93(6–7), pp. 607–08, 1981.

*Primary Examiner*—Paul J. Killos
*Assistant Examiner*—Jean F. Vollano
*Attorney, Agent, or Firm*—Sughrue, Mion, Zinn, Macpeak & Seas, PLLC

[57] ABSTRACT

Ionic compounds represented by general formula (I), method of their production, olefin polymerization catalyst components, and olefin polymerization catalysts containing the components are provided.

$$[M(R^1)_k(R^2)_l(R^3)_m(R^4-L)_n]^-[D]^+ \qquad (I)$$

(wherein, M is an element belonging to the Group 13; $R^1$, $R^2$ and $R^3$ are pentafluorophenyl, etc., $R^4$ is a substituted phenylene group, etc., k, l and m being each 0 or an integer of 1 to 3, and n being an integer of 1 to 4 such that k+l+m+n=4; L is trichlorosilyl, methyldichlorosilyl, dimethylchlorosilyl group, etc.; and D is a monovalent cation). The catalyst of this invention, which is used in combination with the ionic compound of this invention, a carrier, an organometal compound and a Group 4, 5 or 6 transition metal compound, has high activity so that polymerization of olefins by a slurry process, a gas phase process or the like using the catalyst gives rise to a polymer having good powder characteristics and attachment of the polymer to the reactor is minimized.

18 Claims, No Drawings

IONIC COMPOUND AND OLEFIN POLYMERIZATION CATALYST CONTAINING THE SAME

This application is a 371 of PCT/JP96/01514 filed Jun. 5, 1996.

FIELD OF THE INVENTION

This invention relates to ionic compounds, method for preparing the same, olefin polymerization catalyst components containing the same, and olefin polymerization catalyst compositions containing the components.

BACKGROUND OF THE INVENTION

Heretofore, there has been known a method of producing olefins using a metallocene compound and methylaluminoxane as a catalyst in a homogeneous system. For example, Japanese Patent Application Laid-open No. 19309/1983 discloses a method of producing ethylene homopolymers and ethylene/$C_3$–$C_{12}$ α-olefin copolymers using biscyclopentadienyl zirconium dichloride and a linear or cyclic methylaluminoxane as a catalyst. Japanese Patent Application Laid-open No. 130314/1986 discloses a method of producing stereoregular polypropylenes using a catalyst comprising a zirconium compound containing as a ligand a compound having two indenyl groups intervened with an ethylene group and aluminoxane. Also, Japanese Patent Application Laid-open No. 41303/1990 discloses a method of producing poly-α-olefins having a good syndiotacticity.

There have also been proposed catalyst composition systems that use no aluminoxane cocatalyst. Taube et al. performed polymerization of ethylene using a metallocene represented by $[Cp_2TiMe(THF)]^-[BPh_4]^+$ (Cp: a cyclopentadienyl group, Me: a methyl group, THF: a tetrahydrofuranyl group, Ph: a phenyl group) (J. Organometall. Chem., 347, C9 (1988)). In J. Am. Chem. Soc., 109, 4111 (1987), Jordan et al. reported that a zirconium complex represented by $[Cp_2ZrR(L)]^-$ (Cp: a cyclopentadienyl group, R: a methyl group or a benzyl group, L: a Lewis base) functions as a catalyst for polymerization of ethylene. Japanese Patent Application Laid-open Nos. 501950/1989 and 502036/1989 disclose methods of polymerizing olefins using catalysts comprising a cyclopentadienyl metal compound and an ionic compound which can stabilize the cyclopentadienyl metal cations. Zambelli et al. reported that use of a catalyst which comprises a zirconium compound having a cyclopentadiene derivative as a ligand, trimethylaluminum and fluorodimethylaluminum enables production of isotactic polypropylenes (macromolecules, 22, 2186 (1989)).

However, use of the above-described catalysts, when used in slurry system processes or gaseous system processes, caused problems since the polymer is produced in the form of fine powder having a low bulk density and, hence, it is difficult to handle it and the polymer produced attaches to an inner wall of the reactor.

In order to solve these problems, various proposals have been made to have the catalysts carried on solid carriers.

For example, Japanese Patent Application Laid-open Nos. 108610/1986, 296008/1986, 280703/1988, 22804/1988, 51405/1988, 51407/1988, 55403/1988, 61010/1988, 248803/1988, 100808/1992, 74412/1991, 709/1991 and 7306/1992 disclose methods of producing olefins using solid catalysts comprising inorganic metal oxides such as silica, alumina, silica-alumina and the like having carried thereon metallocene compounds and methylaluminoxane, respectively.

Japanese Patent Application Laid-open Nos. 6003/1989, 6004/1989, 6005/1989, 11104/1989 and 11105/1989 disclose methods in which catalysts are used that comprise a metallocene compound and aluminoxane carried on an organometallic magnesium compound.

Also, Japanese Patent Application Laid-open Nos. 260903/1988, 31403/1992 and 74411/1991 disclose polymerization methods in which catalysts are used that comprise a metallocene compound and aluminoxane carried on polymer such as polyethylene, polystyrene, respectively.

Japanese Patent Application Laid-open Nos. 276805/1986 and 74415/1991 disclose polymerization methods using a metal oxide and a metallocene compound having carried thereon only methylaluminoxane.

Further, Japanese Patent Application Laid-open Nos. 259004/1989, 259005/1989, 56928/1994 and 56929/1994 disclose methods in which catalysts are used that comprise a metallocene compound having a special ligand, carried on a porous metal oxide carrier, such as silica. On the other hand, Japanese Patent Application Laid-open No. 234405/1992 discloses a method of solidifying a catalyst using a cyclopentadienyl group bonded to a poly(halogenated methylstyrene) to form a complex with the catalyst.

Studies have been made in order to obtain solidified catalysts for catalyst systems using no aluminoxane cocatalyst. For example, Japanese Patent Application Laid-open No. 234709/1991, 247128/1993, 239138/1993, 148316/1993, 155926/1993 and 502906/1993 disclose methods in which catalysts are used that comprise a cation type metallocene compound reacted with a non-coordinating boron compound carried on an inorganic metal compound such as silica. However, in these carrying methods, the boron compound is not bonded to the carrier so that upon polymerization, activated species come off from the surface of the carrier, causing the resulting resin to attach to the reactor.

Further, Japanese Patent Application Laid-open No. 501573/1995 (WO 93/11172) discloses a method involving use of an ion-activated transient metal catalyst composition useful for the polymerization of olefins, the composition comprising a core portion and a polyanionic transient metal catalyst component, i.e., a polyanion portion comprising a plurality of metal- or metalloid atom-containing non-coordinating anionic group chemically bonded to the core portion as a side chain. Here, the core portion is comprised by (1) an oligomer of a salt of a polymerizable anionic portion containing a metalloid atom and an organic cation prepared in the presence of a metallocene, (2) cross-linked particles of a polymer such as a styrene based polymer, or (3) inorganic particles such as those of glass, silica, metal, etc. In the above-described publication, there are described examples which used the former two ((1), (2)) as the core and confirmed their effect as a polymerization catalyst. However, when the present inventors tested the examples, the method was insufficient in either one of the activity of olefin polymerization, powder characteristics of the resulting polyolefins, and attachment of the polymers to the reactor.

Therefore, an object of this invention is to provide a carrier-supported olefin polymerization catalyst which is excellent in the activity of catalyst and has solved the problem involved in the conventional methods that the resulting polymer attaches to the wall of the reactor and to provide an ionic compound for use therein.

SUMMARY OF THE INVENTION

The present inventors have made intensive research in order to solve the above-described problems and as a result have discovered a Group 13 element (after the 1990 Rule for Nomenclature of Inorganic Compounds)-containing ionic compound having a functional group which is bondable to a carrier and found that highly active polymer which does not attach to the inner wall of the reactor can be obtained by performing polymerization of olefins using an olefin polymerization catalyst comprising a carrier to which the ionic compound is chemically bonded, an organic metal and a transient metal compound belonging to the Group IV, V or VI of the periodic table.

That is, this invention provides the ionic compounds, methods of producing the same, catalyst components for olefin polymerization catalysts, and olefin polymerization catalysts containing the components described below.

1) Ionic compounds represented by general formula (I) below:

$$[M(R^1)_k(R^2)_l(R^3)_m(R^4-L)_n]^-[D]^+ \qquad (I)$$

(wherein, M is an element belonging to the Group 13;

$R^1$, $R^2$ and $R^3$, which may be the same or different, represent each a $C_1$–$C_{20}$ hydrocarbyl group, a substituted hydrocarbyl group, an alkoxide group, or a halogen atom;

R4 represents a $C_1$–$C_{20}$ alkylene group, a substituted alkylene group, a substituted phenylene group, a silanylene group, a substituted silanylene group, a silalkylene group, a substituted silalkylene group, an oxasilanylene group, a substituted oxasilanylene group, or an oxasilalkylene group, with k, l and m being each 0 or an integer of 1 to 3, and n being an integer of 1 to 4 such that k+l+m+n=4;

L is a group represented by general formula (II) or (III) below and is chemically bonded to $R^4$:

$$SiR^5R^6R^7 \qquad (II)$$

$$R^8R^9R^{10}SiYSiR^{11}R^{12} \qquad (III)$$

(wherein $R^5$ to $R^{12}$, which may be the same or different, represent each a $C_1$–$C_{20}$ hydrocarbyl group, a substituted hydrocarbyl group, an alkoxide group, or a halogen atom, with at least one of $R^5$, $R^6$ and $R^7$ and at least one of $R^8$, $R^9$ and $R^{10}$ being a halogen atom;

Y is —O—, a $C_1$–$C_{20}$ alkylene group, a substituted alkylene group, a phenylene group, a substituted phenylene group, or a group represented by formula:

$$-(Z^1SiZ^2Z^3Z^4)_r-$$

(wherein $Z^1$ and $Z^4$, which may be the same or different, represent each an alkylene group, a substituted alkylene group, a phenylene group, a substituted phenylene group, —O—, an oxyalkylene group, a substituted oxyalkylene group, an oxyphenylene group, or a substituted oxyphenylene group; $Z^2$ and $Z^3$, which may be the same or different, represent each a hydrogen atom, an alkyl group, a substituted alkyl group, a phenyl group, or a substituted phenyl group; r is an integer of at least 1););

when n is 2 or more, each $R^4$-L may be the same or different;

D is a monovalent cation selected from the group consisting of carbonium, anilinium, ammonium, ferrocenium, phosphonium, sodium, potassium, or lithium).

2) The ionic compound described in 1) above, wherein n is 1.

3) The ionic compound described in 1) above, wherein M is boron.

4) The ionic compound described in 1) above, wherein $R^1$, $R^2$ and $R^3$ are each a pentafluorophenyl group.

5) The ionic compound described in 1) above, wherein L is a halogenated silyl group, a halogenated substituted silyl group, a halogenated silalkyl group, a halogenated substituted silalkyl group, a halogenated oxasilyl group, a halogenated substituted oxasilyl group, or a halogenated oxasilalkyl group.

6) The ionic compound described in 1) above, wherein $R^4$ is a substituted phenylene group.

7) The ionic compound described in 6) above, wherein $R^4$ is a 2,3,5,6-tetrafluorophenylene group.

8) The ionic compound described in 1) above, wherein L is a trichlorosilyl group, a methyldichlorosilyl group, or a dimethylchlorosilyl group.

9) The ionic compound described in 1) above, wherein D is an anilinium ion.

10) A method of producing ionic compounds represented by general formula (I)

$$[M(R^1)_k(R^2)_l(R^3)_m(R^4-L)_n]^-[D]^+ \qquad (I)$$

(wherein the symbols in the formula have the same meanings as in 1) above) comprising using components represented by (1) to (4) below:

(1) A compound represented by general formula (IV):

$$X^1-R^4-X^2 \qquad (IV)$$

(wherein $X^1$ and $X^2$ independently represent a hydrogen atom or a bromine atom, and $R^4$ has the same meaning as in 1) above);

(2) A compound represented by general formula (V):

$$MR^1R^2R^3 \qquad (V)$$

(wherein M is an element belonging to the Group 13; and $R^1$, $R^2$ and $R^3$, which may be the same or different, represent each a $C_1$–$C_{20}$ hydrocarbyl group, substituted hydrocarbyl group, or alkoxide group or a halogen atom);

(3) A compound represented by general formula (VI) or (VII):

$$SiR^5R^6R^7R^{13} \qquad (VI)$$

$$R^8R^9R^{10}SiYSiR^{11}R^{12}R^{14} \qquad (VII)$$

(wherein $R^5$ to $R^{14}$ have the same meanings as in 1) above); and (4) A halide of a monovalent cation.

11) A method of producing ionic compounds represented by general formula (I)

$$[M(R^1)_k(R^2)_l(R^3)_m(R^4-L)_n]^-[D]^+ \qquad (I)$$

(wherein the symbols in the formula have the same meanings as in 1) above) comprising the steps of:

(a) substituting bromine or hydrogen at the a compound represented by general formula (IV)

$$X^1-R^4-X^2 \qquad (IV)$$

(wherein the symbols in the formula have the same meanings as in 10) above) by lithium with an organic lithium to obtain a lithium substituted compound;

(b) reacting the lithium substituted compound with a Group 13 element containing compound represented by general formula (V)

MR¹R²R³ (V)

(wherein the symbols in the formula have the same meanings as in 10) above) to obtain a lithium compound represented by general formula (VIII)

[M(R¹)ₖ(R²)ₗ(R³)ₘ(R⁴-A)ₙ]⁻[Li]⁺ (VIII)

(wherein A is hydrogen or bromine chemically bonded to R⁴);
(c) lithionating the compound of general formula (VIII) with an organic lithium and then reacting with a silicon compound represented by general formula (VI) or (VII) below:

SiR⁵R⁶R⁷R¹³ (VI)

R⁸R⁹R¹⁰SiYSiR¹¹R¹²R¹⁴ (VII)

(wherein the symbols in the formulae have the same meanings as in 10) above) to obtain a compound represented by general formula (IX)

[M(R¹)ₖ(R²)ₗ(R³)ₘ(R⁴-L)ₙ]⁻[Li]⁺ (IX)

(wherein L has the same meaning as in 1) above and other symbols in the formula have the same meanings as above); and
(d) reacting the compound of general formula (IX) with a halide of a monovalent cation.
12) The method of producing the ionic compounds as described in 10) or 11) above, wherein the compound of general formula (IV) is a compound represented by general formula (IVa)

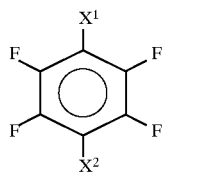

(IVa)

(wherein the symbols in the formula have the same meanings as in 10) above).
13) A Catalyst component for olefin polymerization comprising the ionic compound described in 1) above chemically bonded to a carrier.
14) The catalyst component as described in 13) above, wherein the carrier is a solid having a functional group represented by general formula (X)

—OR (X)

(wherein R is a hydrogen atom, a $C_1$–$C_{20}$ alkyl group, alkali metal or amine).
15) The catalyst component as described in 14) above, wherein the carrier is a solid having a hydroxyl group.
16) The catalyst component as described in 13) above, wherein the carrier is silica, alumina or mixtures thereof.
17) A catalyst for olefin polymerization comprising the following as essential components:

(a) the catalyst component for olefin polymerization as described in 13) above,
(b) an organometal compound, and
(c) a Group 4, 5 or 6 transition metal compound.

18) The catalyst as described in 17) above, wherein the Group 4, 5 or 6 transition metal compound is metallocene.

DETAILED DESCRIPTION OF THE INVENTION

Hereafter, this invention will be described in detail.
[IONIC COMPOUND]
The ionic compound which can be used in this invention includes those compounds represented by the following general formula (I):

[M(R¹)ₖ(R²)ₗ(R³)ₘ(R⁴-L)ₙ]⁻[D]⁺ (I)

wherein M is a Group 13 metal. Preferred examples of M include boron and aluminum, with boron being particularly preferred.

$R^1$, $R^2$ and $R^3$ (each bonded to M), which may be the same or different, are selected from a $C_1$–$C_{20}$ hydrocarbyl group, substituted hydrocarbyl group, or alkoxide group or a halogen atom. These are preferably a $C_1$–$C_{20}$ aromatic hydrocarbyl group, halogen-substituted aromatic hydrocarbyl group, or halogenated hydrocarbon-substituted aromatic hydrocarbyl group, and more preferably a phenyl group, a 2-fluorophenyl group, a 3-fluorophenyl group, a 4-fluorophenyl group, a 2,4-difluorophenyl group, a 2,5-difluorophenyl group, a 3,5-difluorophenyl group, a 3,4,5-trifluorophenyl group, a 2,3,4,5-tetrafluorophenyl group, a pentafluorophenyl group, or a 3,5-bis(trifluoromethyl) phenyl group, with a pentafluorophenyl group being most preferred.

k, l and m are each 0 or an integer of 1 to 3, provided that they have a relation with n described below such that k+l+m+n=4.

$R^4$ (bonded to M) represents a $C_1$–$C_{20}$ alkylene group, substituted alkylene group, substituted phenylene group, silanylene group, substituted silanylene group, silalkylene group, substituted silalkylene group, oxasilanylene group, substituted oxasilanylene group, or oxasilalkylene group.

The present inventors confirmed that the substituent groups of particularly the substituted phenylene group represented by $R^4$ give important influence to the activity of the catalyst and the properties of the resulting polymer and that preferred substituents for phenylene are halogens and halogenated hydrocarbons. Preferred substituted phenylene groups include 2-fluorophenyl group, 3-fluorophenyl group, 2,5-difluorophenyl group, 3,5-difluorophenyl group, 2,3,5-trifluorophenyl group, 3,5-bis(trifluoromethyl)phenylene group, 2,3,5,6-tetrafluorophenyl group, among which 2,3,5,6-tetrafluorophenyl group is particularly preferred.

L (bonded to R4) is a carrier bondable functional group. The carrier bondable functional group is a functional group which can form a chemical bond with a surface of a carrier. For example, when there is a hydroxyl group on the surface of a carrier, a compound having a chlorosilyl group can form a silicon-oxygen bond by a reaction with the hydroxyl group. In this case, the chlorosilyl group is a carrier bondable functional group. More specifically, the carrier bondable functional group includes those functional groups represented by general formulae (II) or (III) below:

SiR⁵R⁶R⁷ (II)

R⁸R⁹R¹⁰SiYSiR¹¹R¹² (III)

(wherein $R^5$ to $R^{12}$ (each bonded to Si), which may be the same or different, represent each a $C_1$–$C_{20}$ hydrocarbyl group, substituted hydrocarbyl group, or alkoxide group, or a halogen atom, with at least one of $R^5$, $R^6$ and $R^7$ and at least one of $R^8$, $R^9$ and $R^{10}$ being a halogen atom;

Y is —O—, a $C_1$–$C_{20}$ alkylene group, substituted alkylene group, phenylene group, substituted phenylene group, or a group represented by formula:

—(Z$^1$SiZ$^2$Z$^3$Z$^4$)$_r$—

(wherein Z$^1$ and Z$^4$, which may be the same or different, represent each an alkylene group, a substituted alkylene group, a phenylene group, a substituted phenylene group, —O—, an oxyalkylene group, a substituted oxyalkylene group, an oxyphenylene group, or a substituted oxyphenylene group; Z$^2$ and Z$^3$, which may be the same or different, represent each a hydrogen atom, an alkyl group, a substituted alkyl group, a phenyl group, or a substituted phenyl group; r is an integer of at least 1).

Specific examples of L include a trichlorosilyl group, a methyldichlorosilyl group, a dimethylchlorosilyl group, an ethyldichlorosilyl group, a diethylchlorosilyl group, a phenyldichlorosilyl group, a diphenylchlorosilyl group, a trimethoxysilyl group, a methyldimethoxysilyl group, a dimethylchlorosilyl group, an ethyldimethoxysilyl group, a diethylmethoxysilyl group, a triethoxysilyl group, a methyldiethylsilyl group, a dimethylethoxysilyl group, an ethyldiethoxysilyl group, a diethylethoxysilyl group, a phenyldiethoxysilyl group, a diphenylethoxysilyl group, a trihydroxysilyl group, a dihydroxyphenylsilyl group, a 2-(dimethylchlorosilyl)ethyldimethylsilyl group, a 6-(dimethylchlorosilyl)hexyldimethylchlorosilyl group, a 8-(dimethylchlorosilyl)octyldimethylchlorosilyl group, a 2-(trichlorosilyl)ethyldichlorosilyl group, a 6-(trichlorosilyl)hexyldichlorosilyl group, a 8-(trichlorosilyl)octyldichlorosilyl group, etc. of these, a trichlorosilyl group, a trimethoxysilyl group, triethoxysilyl group, a trihydroxysilyl group, a dimethylchlorosilyl group, a dimethylmethoxysilyl group, a dimethylethoxysilyl group, a dimethylhydroxysilyl group, a methyldichlorosilyl group, a methyldimethoxysilyl group, a methyldiethoxysilyl group, and a methyldihydroxysilyl group are preferred, with a trichlorosilyl group, a methyldichlorosilyl group, and a dimethylchlorosilyl group being particularly preferred.

n is an integer of 1 to 4, and when n is 2 or more, R$^4$–L's may be a combination of different groups.

D represents a monovalent cation, which means carbonium, anilinium, ammonium, ferrocenium, phosphonium, sodium, potassium, lithium, etc.

Specific examples of D include trimethylammonium, triethylammonium, tripropylammonium, tributylammonium, N,N-dimethylammonium, N,N-diethylammonium, N,N-2,4,5-pentamethylanilinium, triphenylphosphonium, tri(p-tolyl)phosphonium, triphenylcarbenium, etc. Of these, N,N-dimethylanilinium and triphenylcarbenium are preferred.

Specific examples of such an ionic compound include N,N-Dimethylanilinium salts, for example, the following compounds.

N,N-Dimethylanilinium tris(pentafluorophenyl) p-trichlorosilyltetrafluorophenylborate,
N,N-Dimethylanilinium tris(pentafluorophenyl) p-methyldichlorosilyltetrafluorophenylborate,
N,N-Dimethylanilinium tris(pentafluorophenyl) p-dimethylchlorosilyltetrafluorophenylborate,
N,N-Dimethylanilinium tris(pentafluorophenyl) p-trimethoxysilyltetrafluorophenylborate,
N,N-Dimethylanilinium tris(pentafluorophenyl) p-dimethoxymethylsilyltetrafluorophenylborate,
N,N-Dimethylanilinium tris(pentafluorophenyl) p-methoxydimethylsilyltetrafluorophenylborate,
N,N-Dimethylanilinium tris(pentafluorophenyl) p-triethoxysilyltetrafluorophenylborate,
N,N-Dimethylanilinium tris(pentafluorophenyl) p-diethoxymethylsilyltetrafluorophenylborate,
N,N-Dimethylanilinium tris(pentafluorophenyl) p-ethoxydimethylsilyltetrafluorophenylborate,
N,N-Dimethylanilinium tris(pentafluorophenyl) p-trihydroxysilyltetrafluorophenylborate,
N,N-Dimethylanilinium tris(pentafluorophenyl) p-dihydroxymethylsilyltetrafluorophenylborate,
N,N-Dimethylanilinium tris(pentafluorophenyl) p-hydroxydimethylsilyltetrafluorophenylborate,
Triphenylcarbenium tris(pentafluorophenyl) p-trichlorosilyltetrafluorophenylborate,
Triphenylcarbenium tris(pentafluorophenyl) p-methyldichlorosilyltetrafluorophenylborate,
Triphenylcarbenium tris(pentafluorophenyl) p-dimethylchlorosilyltetrafluorophenylborate,
Triphenylcarbenium tris(pentafluorophenyl) p-trimethoxysilyltetrafluorophenylborate,
Triphenylcarbenium tris(pentafluorophenyl) p-dimethoxymethylsilyltetrafluorophenylborate,
Triphenylcarbenium tris(pentafluorophenyl) p-methoxydimethylsilyltetrafluorophenylborate,
Triphenylcarbenium tris(pentafluorophenyl) p-triethoxysilyltetrafluorophenylborate,
Triphenylcarbenium tris(pentafluorophenyl) p-diethoxymethylsilyltetrafluorophenylborate,
Triphenylcarbenium tris(pentafluorophenyl) p-ethoxydimethylsilyltetrafluorophenylborate,
Triphenylcarbenium tris(pentafluorophenyl) p-trihydroxysilyltetrafluorophenylborate,
Triphenylcarbenium tris(pentafluorophenyl) p-dihydroxymethylsilyltetrafluorophenylborate,
Triphenylcarbenium tris(pentafluorophenyl) p-hydroxydimethylsilyltetrafluorophenylborate, Of these ionic compounds, preferred are N,N-dimethylanilinium tris(pentafluorophenyl) 4-(trichlorosilyl)-2,3,5,6-tetrafluorophenylborate, N,N-dimethylanilinium tris(pentafluorophenyl) 4-(methyldichlorosilyl)-2,3,5,6-tetrafluorophenylborate, and N,N-dimethylanilinium tris (pentafluorophenyl) 4-(dimethylchlorosilyl)-2,3,5,6-tetrafluorophenylborate.

[Production Method for Ionic Compounds]

The ionic compounds of this invention can be produced using the following compounds.

(1) A compound represented by general formula (IV):

$$X^1\text{–}R^4\text{–}X^2 \tag{IV}$$

(wherein $X^1$ and $X^2$ independently represent a hydrogen atom or a bromine atom, and $R^4$ has the same meaning as above);

(2) A compound represented by general formula (V):

$$MR^1R^2R^3 \tag{V}$$

(wherein M, $R^1$, $R^2$ and $R^3$ have the same meanings as above);

(3) A compound represented by general formula (VI) or (VII):

$$SiR^5R^6R^7R^{13} \tag{VI}$$

$$R^8R^9R^{10}SiYSiR^{11}R^{12}R^{14} \tag{VII}$$

(wherein $R^5$ to $R^{12}$ have the same meanings as above, and $R^{13}$ and $R^{14}$ independently represent a $C_1$–$C_{20}$ hydrocarbyl group, substituted hydrocarbyl group, alkoxide group, or a halogen atom); and (4) A halide of a monovalent cation.

As the reaction process for producing these compounds, there may be considered various reaction procedures. However, any process may be used as far as there can finally be obtained compounds represented by general formula (I)

$$[M(R^1)_k(R^2)_l(R^3)_m(R^4-L)_n]^-[D]^+ \quad \text{(I)}$$

(wherein the symbols in the formula have the same meanings as above).

As the most typical process, there can be cited a reaction process including the following steps (a) to (d). This reaction process, described briefly, comprises the steps of activating a compound containing a $R^4$ group (first step), bonding the compound with a compound containing a Group 13 element (M) (second step), introducing a carrier bondable functional group to the resulting compound (L) (third step), and then forming a salt with a cation $[D]^+$ (fourth step).

Hereafter, each of the steps is described in detail.

(a) First step:

Bromines or hydrogens in a compound represented by general formula (IV)

$$X^1-R^4-X^2 \quad \text{(IV)}$$

(wherein $X^1$ and $X^2$ are bromine or hydrogen provided that for compounds having low acidities, at least one of the symbols must be bromine) are substituted by lithium (lithionated) with an organic lithium.

The lithionation can be performed by a conventional method. More specifically, the compound of formula (IV) above and an organic lithium compound are mixed in a nonreactive solvent to allow reaction therebetween.

The compound of formula (IV) is selected depending on final target compound and is preferably a halogenated aryl or a halogenated hydrocarbon-substituted aryl as described above. Particularly preferred are tetrafluoro-mono- (or -di) -bromobenzene represented by the following formula (IVa)

Any organic lithium compounds may be used without limitation as far as they are commonly used for lithionation. For example, there can be cited n-butyllithium, t-butyllithium, and phenyllithium. It is preferred that they are dissolved in an inert solvent such as hexane before they can be subjected to lithionation. Preferred reaction solvents include ether based solvents such as diethyl ether and tetrahydrofuran.

The reaction between the compound of formula (IV) and the organic lithium compound can be performed in proportions of about 1:1 to 1:10 (by mole), and preferably 1:1 (by mole). The reaction temperature is −100° to 0° C., and preferably −80° to −20° C. It is preferred to allow the reaction to proceed gently by adding the organic lithium compound in portions. The reaction time lasts preferably for 30 minutes or longer.

(b) Second step: Formation of a salt containing a Group 13 element-containing compound The lithium substituted compound obtained in the first step is reacted with a Group 13 element-containing compound represented by general formula (V)

$$MR^1R^2R^3 \quad \text{(V)}$$

(wherein the symbols in the formula have the same meanings as above) to obtain a lithium compound represented by general formula (VIII)

$$[M(R^1)_k(R^2)_l(R^3)_m(R^4-A)_n]^-[Li]^+ \quad \text{(VIII)}$$

(wherein A is hydrogen or bromine).

In the formula (V) above, M is a Group 13 element, among which preferred are boron and aluminum, with particularly preferred being boron. In the same formula, $R^1$, $R^2$ and $R^3$, which may be the same or different, may be a C1–C20 hydrocarbyl group, substituted hydrocarbyl group, or alkoxide group, or a halogen atom. Preferably, they represent a phenyl group, a 2-fluorophenyl group, a 3-fluorophenyl group, a 4-fluorophenyl group, a 2,4-difluorophenyl group, a 2,5-difluorophenyl group, a 3,5-difluorophenyl group, a 3,4,5-trifluorophenyl group, a 2,3,4,5-tetrafluorophenyl group, a pentafluorophenyl group, a 3,5-bis(trifluoromethyl)phenyl group, with a pentafluorophenyl group being particularly preferred.

This reaction can be performed by mixing the lithionated compound obtained in the first step with a solution of the compound of general formula (V) in a solvent in proportions such that the molar ratio of the lithionated compound to the compound of general formula (V) is 1.0 or more. Preferred mixing ratio is 1.0 to 2.0. When the lithionated compound is added, it is preferred that the temperature of the solution is kept low. More specifically, the temperature is −100° to 50° C., and preferably −20° to 30° C. As for the solvent for dissolving the compound of general formula (V), there can be used liquids which are nonreactive with the lithionated compound and the compound of general formula (V). Preferred solvent includes $C_{10}$–$C_{20}$ hydrocarbons and ethers. Particularly preferred ones are toluene, heptane, decane, isoparaffin, diethyl ether, and tetrahydrofuran. The reaction time is preferably 30 minutes or longer. It is preferred that after the reaction, unreacted materials are removed by washing or the like. The compound of general formula (V) may be used in the state where a solvent such as ether is added.

(c) Third step: Introduction of Carrier Bondable Functional Group

The compound of general formula (VIII) is lithionated with an organic lithium and then reacted with a silicon compound represented by general formula (VI) or (VII) below $$SiR^5R^6R^7R^{13} \quad \text{(VI)}$$

$$R^8R^9R^{10}SiYSiR^{11}R^{12}R^{14} \quad \text{(VII)}$$

(wherein $R^5$ to $R^{12}$ have the same meanings as above, and $R^{13}$ and $R^{14}$ independently represent a $C_1$–$C_{20}$ hydrocarbyl group, substituted hydrocarbyl group, alkoxide group, or a halogen atom) to obtain a compound represented by general formula (IX)

$$[M(R^1)_k(R^2)_l(R^3)_m(R^4-L)_n]^-[Li]^+ \quad \text{(IX)}$$

(wherein the symbols in the formula have the same meanings as above).

The mixing ratio of the compound of general formula (VIII) and the silicon compound, as molar ratio of the latter to the former, is 1 fold to 100 folds, preferably 2 folds to 20 folds. Stirring is performed for a certain time at room temperature to complete the reaction. Thereafter, a hydrocarbon having a boiling point higher than the solvent is added to the reaction mixture, the reaction solvent is distilled off, and the hydrocarbon solvent is removed. After washing with the hydrocarbon solvent, the washing solvent is removed. The compound thus obtained is dissolved in a solvent such as dichloromethane.

(d) Fourth step: Cation Exchange Reaction

Finally, the compound of general formula (IX) is reacted with a halide of a cation D to yield a target ionic compound represented by general formula (I)

$$[M(R^1)_k(R^2)_l(R^3)_m(R^4-L)_n]^-[D]^+ \quad (I)$$

(wherein the symbols in the formula have the same meanings as above).

The halide of D is a compound which generates a monovalent cation D when reacted with the compound of general formula (IX) above. More specifically, the halide of D includes trimethylamine hydrochloride, triethylamine hydrochloride, tripropylamine hydrochloride, tributylamine hydrochloride, N,N-dimethylaniline hydrochloride, N,N-diethylamine hydrochloride, N,N-2,4,5-pentamethylaniline hydrochloride, triphenylphosphine hydrochloride, triphenylchloromethane and the like. Of these, preferred are N,N-dimethylaniline hydrochloride and triphenylchloromethane.

The reaction can be performed at −100° to 200° C., preferably at 20° to 150° C. The reaction time is preferably 1 hour or longer. Lithium halide precipitates and removal of which yields the target compound. The compound can be used in a state of solution or in a state of solid after drying.

[Catalyst Component for Olefin Polymerization]

Next, description will be made of the catalyst component for olefin polymerization, comprising the ionic compound of this invention chemically bonded to a carrier.

In this invention, by the term "chemical bonds" is meant covalent bonds, ionic bonds, metal bonds, and coordination bonds.

(1) Carrier

In this invention, by the term "carrier" is meant a solid which has a surface with which a plurality of the ionic compounds of this invention can form chemical bonds, the surface having an area and properties such that upon polymerization reaction, a plurality of polymerization active sites can be formed.

As the carrier, there can be used inorganic oxides, inorganic chlorides, inorganic hydroxides, organic high molecular weight compounds. More specifically, there can be used one or more members selected from the group consisting of inorganic compounds such as silica, alumina, silica-alumina, magnesia, titania, zirconia, and calcia, polymers of vinyl chloride, vinyl alcohol, methacrylic acid, acrylic acid and the like, or copolymers thereof with styrene, divinylbenzene or the like, and homopolymer or copolymer of α-olefins chemically modified to have a functional group which can react with a carrier bondable functional group of the ionic compound to form a chemical bond to the ionic compound. It is preferred to use one or more of silica, alumina or silica-alumina.

Among the carriers, preferred are those having a functional group represented by general formula (x)

$$-OR \quad (X)$$

on the surface of the carrier.

In the above formula, R represents hydrogen, a $C_1$–$C_{20}$ alkyl group, alkali metal or amine. Of these, preferred are hydrogen, a methyl group, an ethyl group, sodium and lithium, with hydrogen being most preferred.

The carrier in this invention requires large surface area and pore diameter and functional groups on the surface for chemically modifying the surface with an ionic compound. Further, the ionic compound borne form polymerization active species by forming ion pairs with the transition metal compound so that the carrier must have space for forming such ion pairs. In addition, polymerization activity per catalyst is higher, the larger the amount of the ion pair formed on the carrier and, hence, it is desired that the carrier have a large surface area and a large average pore diameter. As the carrier in this invention, it is preferred to use fine particles having an average particle diameter of 5 to 200 μm, a specific surface area of 100 to 1,000 m²/g, and an average pore diameter of 20 Å or more.

(2) Reaction of the Ionic Compound with the Carrier

The reaction between the carrier in this invention and the ionic compound having a carrier bondable functional group can be performed by various methods. Generally, the reaction is performed in organic solvents. More specifically, there can be used aliphatic hydrocarbons such as pentane, hexane, heptane, octane, nonane, and decane, alicyclic hydrocarbons such as methylcyclopentane, cyclopentane, and cyclooctane, aromatic hydrocarbons such as benzene, toluene, xylene, cumene, and cymene, aliphatic halogenated hydrocarbons such as chloroform and dichloromethane, aromatic halogenated hydrocarbons such as chlorobenzene, and dichlorobenzene, alcohols such as methanol and ethanol, ethers such as diethyl ether and tetrahydrofuran, and the like.

Although the reaction between the carrier and the ionic compound having a carrier bondable functional group can be under any conditions as far as the target bond is formed, generally the following conditions are desirable.

The reaction temperature is usually −70° C. to 200° C., and preferably 0° C. to 150° C. It is preferred that the reaction between the ionic compound having a carrier bondable functionality with the functional group on the surface of the carrier proceed sufficiently.

The reaction time may vary depending on the concentration, temperature and other conditions and is not limited generally. Usually, the reaction can proceed for 1 to 50 hours.

The reaction for bonding can be carried out at a concentration of the ionic compound in the reaction solvent being 1 to 10,000 ppm and at a concentration of the carrier being 1 to 50 wt. %.

There is no particular limitation in the proportion of amounts of the ionic compound having a carrier bondable functional group and of the carrier. When the number of the functional groups on the surface of the carrier is equal to or greater than the equivalent the carrier bondable functional group, unreacted functional groups on the surface of the carrier will react with the transient metal compound so that there is the possibility that no polymerization active species can be formed. In this case, the reaction with the transient metal compound can be prevented from occurring by reacting the functional group on the surface of the carrier with a different compound. For example, where the unreacted functional group is a hydroxyl group, treatment of the hydroxyl group with trimethylchlorosilane or the like results in the prevention of the reaction between the transient metal compound and the unreacted functional group on the surface of the carrier.

The catalyst component for olefin polymerization, the reaction product, is separated from the reaction mixture and the ionic compounds having unreacted carrier bondable functional groups are removed by washing. As the solvent for washing, there can be used the above-described organic solvents. The temperature for washing is −30° C. to 120° C., and preferably 0° C. to 100° C. Preferably, the washing is continued until the ionic compound having a carrier bondable functional group cannot detected substantially in the washings. After completion of the washing, the solid component carrying the ionic compounds is dried or may be used in the presence of an organic solvent.

Formation of chemical bonds between the ionic compound having a carrier bondable functional group and the carrier can be confirmed by determination of a reduction in the amount of the functional group on the carrier as a result of the reaction or by determination of the amount of the compound which is formed as a result of the reaction between the functional group on the surface of the carrier and the carrier bondable functional group of the ionic compound. Alternatively, such is confirmed by detecting IR absorption and NMR peaks of new bonds which are formed as a result of the reaction.

[Catalyst for Olefin Polymerization]

Next, description will be made of the catalyst for olefin polymerization of this invention.

The component for olefin polymerization catalyst is characterized by using (a) a component of olefin polymerization catalyst in which the ionic compound is chemically bonded to the carrier, (b) an organometal compound, and (c) a Group 4, 5 or 6 transtion metal compound.

Of these, (a) has already been described above.

In the organometal compound (component (b)) which is one of the catalyst component for olefin polymerization in this invention, the metal element is generally lithium, sodium, magnesium, aluminum, tin, zinc or titanium. The organic group which combines with the metal to form an organic metal compound generally includes an alkyl group ($C_1$–$C_{10}$), and a phenyl group, a cyclopentadienyl group or derivatives thereof.

At least one of the valence of the above-described metal element must be satisfied with the above-described organic group while the rest valences may be satisfied with other atoms or atomic groups. Such atoms or atomic groups may be, for example, a halogen atom, a hydrogen atom, an alkoxy group, etc.

As such organic compounds, there can be cited, for example, organolithium compounds such as n-butyllithium, t-butyllithium, and phenyllithium, organosodium compounds such as cyclopentadienylsodium and methylsodium, organomagnesium compounds such as butylethylmagnesium, butyloctylmagnesium, ethylmagnesium bromide, and butylmagnesium bromide, organoaluminum compounds such as trimethylaluminum, triethylaluminum, triisobutylaluminum, diethylaluminum halide, diethylaluminum chloride, diethylaluminum bromide, diethylaluminum ethoxide, ethylaluminum sesquichloride, and isobutylaluminoxane, organotin compounds such as tetraethyltin, tetrabutyltin, tributyltin chloride, and tetraphenyltin, organozinc compounds such as diethylzinc, and dibutylzinc, organotitanium compounds such as dicyclopentadientyltitanium dimethyl. Of these, preferred are oragnoaluminum compounds and organomagnesium compounds.

In the catalyst for olefin polymerization of this invention, the orgaometal compound component may be used as a combination of two or more of them.

The Group 4, 5 or 6 transtion metal compound (component (c)), one of the components for olefin polymerization catalyst, is preferably a transtion metal compound represented by general formulae (XI), (XII) or (XIII) below

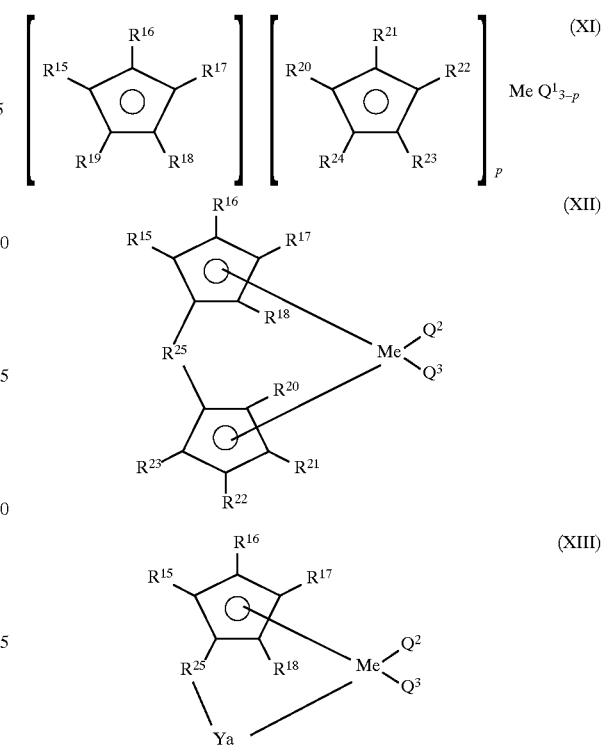

[wherein $R^{15}$ to $R^{24}$, which may be the same or different, represent each a hydrogen atom or a hydrocarbyl group ($C_1$–$C_{20}$ alkyl, alkenyl, aryl, alkylaryl, arylalkyl or the like), an alkylsilyl group, an alkylgermyl group, or a 4–6 membered ring having a carbon-carbon bond, which may be the same or different, $R^{25}$ represents a $C_1$–$C_{20}$ alkylene group, an alkylgermylene or alkylsilylene, a plurality of $Q^1$s, and $Q^2$ and $Q^3$, which may be the same or different, represent each a $C_{1-C20}$ aryl, alkyl, alkenyl, alkylaryl, arylalkyl or the like hydrocarbyl group, alkoxy, alkoxy, siloxy, hydrogen or halogen, Ya is an electron donating ligand selected from —O—, —S—, —$NR^{26}$—, —$PR^{26}$—, or —$OR^{26}$, —$SR^{26}$, —$NR^{26}R^{27}$, and —$PR^{26}R^{27}$ ($R^{26}$ and $R^{27}$ represent each hydrogen or a $C_1$–$C_{20}$ alkyl, alkenyl, aryl, alkylaryl, arylalkyl or the like hydrocarbyl group, or halogenated alkyl or halogenated aryl), Me is a transtion metal of Group 3, 4, 5 and 6 of the periodic table, p is 0 or 1].

In the above formulae, the transtion metal elements of Group 4, 5 and 6 of the periodic table (Group being after 1990 Rule of Inorganic Compound Nomenclature) are preferably selected from the transtion metal elements of Group 4 of the periodic table, i.e., titanium, zirconium, and hafnium, with particularly preferred being zirconium and hafnium.

In the above formulae, the hydrocarbyl group represented by $R^{15}$ to $R^{24}$ include, for example, a methyl group, an ethyl group, a propyl group, a butyl group, an isobutyl group, a t-butyl group, an amyl group, an isoamyl group, a hexyl group, a heptyl group, an octyl group, a nonyl group, a decyl group, a cetyl group, a phenyl group, etc., the alkylsilyl group includes a trimethylsilyl group, etc., the alkylgermyl group includes a trimethylgermyl group, etc. As the cyclopentadienyl ligand, there can be cited, for example, alkyl substituted cyclopentadienyl group such as a cyclopentadienyl group, a methylcyclopentadienyl group, an ethylcyclopentadienyl group, an n-butylcyclopentadienyl group, a t-butylcyclopentadienyl group, a trimethylsilylcyclopentadienyl group, a dimethylcyclopentadienyl group, a pentamethylcyclopentadienyl group, and an indenyl group, a fluorenyl group and the like having or not having similar substituents.

In the above formulae, as the alkylene group represented by $R^{25}$, there can be cited, for example, a methylene group, an ethylene group, a propylene group, an isopropylidene group, a cyclopentylidene group, a cyclohexylidene group, a tetrahydropyran-4-ylidene group, a diphenylmethylene group, etc. As the alkylsilylene group, there can be cited, for example, a dimethylsilylene group, a diphenylsilylene group, etc. As the alkylgermylene group, there can be cited, for example, a dimethylgermylene group, a diphenylgermylene group, etc.

In the above formulae, specific examples of $R^{26}$ and $R^{27}$ in Ya include a methyl group, an ethyl group, a propyl group, a butyl group, an isobutyl group, a t-butyl group, an amyl group, an isoamyl group, a hexyl group, a heptyl group, an octyl group, a nonyl group, a decyl group, a cetyl group, a phenyl group, a benzyl group, etc.

In Ya, ligands of the type $—NR^{26}—$ or $—PR^{26}—$ are preferred.

Hereafter, specific examples of the transtion metal compound represented by general formulae (XI), (XII) or (XIII) when Me is zirconium are exemplified.

Examples of the transition metal compounds represented by general formula (XI) include:

Biscyclopentadienylzirconium dichloride,
Bis(methylcyclopentadienyl)zirconium dichloride,
Bis(n-butylcyclopentadienyl)zirconium dichloride,
Bis (n-butylcyclopentadienyl) zirconium dimethyl,
Bis (1, 3-dimethylcyclopentadienyl) zirconium dichloride,
Bis(pentamethylcyclopentadienyl)zirconium dichioride,
(Cyclopentadienyl)(methylcyclopentadienyl) zirconium di chloride,
(Cyclopentadienyl)(n-butylcyclopentadienyl)zirconium dichloride,
(Cyclopentadienyl)(indenyl)zirconium dichloride,
(Cyclopentadienyl)(fluorenyl)zirconium dichloride,
Cyclopentadienylzirconium trichloride,
Cyclopentadienylzirconium trimethyl,
Pentamethylcyclopentadienylzirconium trichloride,
Pentamethylcyclopentadienylzirconium trimethyl, etc.

Examples of the transtion metal compound represented by general formula (XII) include:

Dimethylsilylenebis(methylcyclopentadienyl)zirconium dichloride,
Isopropylidenebis(methylcyclopentadienyl) zirconium dichloride,
Ethylenebis(indenyl)zirconium dichloride,
Ethylenebis(4,5,6,7-tetrahydro-1-indenyl)zirconium dichloride,
Isopropylidene(cyclopentadienyl)(fluorenyl)zirconium dichloride,
Isopropylidene(cyclopentadienyl)(indenyl)zirconium dichloride,
Isopropylidene(t-butylcyclopentadienyl) t-butylindenyl) zirconium dichloride,
Isopropylidene(t-butylcyclopentadienyl) (t-butylindenyl) zirconiumdimethyl,
Dimethylsilylene-bis{1-(2-methyl-4-benzoindenyl)}-zirconium dichloride,
Dimethylsilylene-bis{1-(2-methyl-4-phenylindenyl)}-zirconium dichloride,
Dimethylsilylene-bis{1-(2-methyl-4-naphthylindenyl)}-zirconium dichloride, etc.

Examples of the transtion metal compound represented by general formula (XIII) include:

Ethylene(t-butylamide)(tetramethylcyclopentadienyl)-zirconium dichloride,
Ethylene(methylamide)(tetramethylcyclopentadienyl)-zirconium dichloride,
Dimethylsilylene(t-butylamide)(tetramethylcyclopentadienyl)zirconium dichloride,
Dimethylsilylene(t-butylamide)(tetramethylcyclopentadienyl)zirconium dibenzyl,
Dimethylsilylene(benzylamide)(tetramethylcyclopentadienyl)zirconium dibenzyl,
Dimethylsilylene(phenylamide)(tetramethylcyclopentadienyl)zirconium dichloride, etc.

Herein, the zirconium compounds were exemplified by referring to their specific names. Also, those transtion metal compounds in which zirconium is replaced by hafnium or titanium are useful in this invention.

Regarding the use of the transtion metal compounds according to this invention, the above-described transtion metal compounds can be used singly or two or more of them may be used in combination.

Molar ratio of the transtion metal compound and the Group 13 element in the components (a), (b) and (c) for olefin polymerization in this invention is such that upon polymerization, the transtion metal is 0.01 to 10 times, preferably 0.1 to 1 time, as much as the Group 13 element. The concentration of the transient metal compound upon polymerization can be 0.01 to 100 ppm, preferably 0.1 to 10 ppm.

The catalyst for olefin polymerization of this invention can be used by contacting (a), (b) and (c) recited in the claims in a solvent or in the presence of a monomer. Methods for contacting the components are not limited particularly. However, a method is preferred in which the component (a) is contacted with the component (b) in an inert solvent and then mixed with the component (c).

Also, after the components (a), (b) and (c) are contacted, the solvent may be distilled off. Alternatively, the mixture may be washed with a solvent such as a hydrocarbon and can be used as a slurry or the solvent may be distilled off thereafter.

The catalyst thus prepared is charged in a polymerization apparatus. In this case, it is preferred that the above-described organometal compound is charged in the polymerization reactor in advance. Particularly when no washing with a hydrocarbon solvent is performed, it is preferred to charge the organometal compound (e.g., organolithium compound) in the polymerization reactor in advance.

[Polymerization of Olefins Using the Catalyst]

In this invention, methods and conditions of polymerization using the above-described catalyst are not limited particularly and there can be used, for example, solution polymerization methods, melt polymerization methods, slurry polymerization methods, suspension polymerization methods, gas phase polymerization methods and the like. This invention is effective particularly for processes in which polymers are non-homogeneous. More specifically, slurry methods and gas phase methods are exemplified.

The polymerization temperature is within the ranges of $-100°$ to $300°$ C., and preferably $0°$ to $150°$ C., and the polymerization pressure is within the ranges of atmospheric pressure to 100 kg/cm$^2$, and preferably atmospheric pressure to 50 kg/cm$^2$. The polymerization reaction may be any of batch methods, semi-continuous methods, and continuous methods. Further, multi-step polymerization can also be performed.

The molecular weight of the resulting polymer can be controlled by use of a chain transfer agent such as hydrogen or polymerization temperature.

In this invention, as the hydrocarbon solvent which can be used in the polymerization, there can be cited, for example, aliphatic hydrocarbons such as propane, butane, isobutane, pentane, hexane, heptane, octane, nonane, and decane, alicyclic hydrocarbons such as methylcyclopentane, cyclopentane, and cyclooctane, aromatic hydrocarbons such as benzene, toluene, xylene, cumene and cymene. These solvents may be used singly or two or more of them can be used in admixture.

As the olefin to be used for polymerization, there can be cited, for example, ethylene, propylene, 1-butene, 3-methyl-1-butene, 1-hexene, 4-methyl-1-pentene, 1-octene, 1-decene, 1-dodecene, 1-tetradecene, 1-hexadecene, 1-octadecene, 1-eicosene, cyclopentene, cycloheptene, norbornene, 5-methyl-2-norbornene, tetracyclododecene, etc. Further, there can be cited, for example, styrene, vinylcyclohexane, vinylcyclohexene, divinylbenzene, dienes, etc.

In this invention, not only homopolymerization of olefins can be performed but also copolymers of, for example, ethylene with propylene, ethylene with 1-butene, and the like can be produced.

In the polymerization method of this invention, preliminary polymerization can be performed using the catalyst of this invention. There is no particular limitation on the method of the preliminary polymerization but known methods can be used therefor. Olefins to be used for preliminary polymerization are not limited particularly and the above-described olefins can be used. The temperature for preliminary polymerization is usually −20° to 300° C., preferably −10° to 200° C., and more preferably 0° to 100° C. As the solvent, there can be used inert hydrocarbons, aliphatic hydrocarbons, aromatic hydrocarbons, monomers and the like. Preferred are aliphatic hydrocarbons. Also, the preliminary polymerization can be performed without solvents.

The catalyst containing the ionic compound carrying carrier of this invention has high activity so that polymerization of olefins by a slurry process, a gas phase process or the like using the catalyst gives rise to a polymer having good powder characteristics and attachment of the polymer to the reactor is minimized.

BEST MODE FOR CARRYING OUT THE INVENTION

Hereafter, this invention will be described in more detail by examples and comparative examples. However, this invention is not limited to the examples. In the following examples, "%" is by weight unless otherwise indicated specifically.

EXAMPLE 1

Production of Dimethylanilinium 4-trichlorosilyl-2,3,5,6-tetrafluorophenyltris(pentafluorophenyl)borate [Ionic Compound]

3.85 Grams (1.86 mmol) of 1-bromo-2,3,5,6-tetrafluorobenzene was dissolved in 50 ml of diethyl ether and cooled in a dry ice/denatured alcohol bath. To the solution was added dropwise 10.5 ml of a solution of 1.6 mol of n-butyllithium/liter of hexane, followed by stirring for 30 minutes to prepare a lithionated product of 1-bromo-2,3,5,6-tetrafluorobenzene (2,3,5,6-tetrafluoropheny-lithium).

The reaction mixture containing the above-described lithionated compound was added to 200 ml of a hexane solution containing 5.07 g (9.9 mmol) of tris(pentafluorophenyl)borane, and stirred at 25° C. for 20 minutes to precipitate product (A). The solution layer was removed and vacuum dried after it was washed with hexane.

1.66 Grams of the product (A) was dissolved in 10 ml of tetrahydrofuran and cooled in a dry ice/denatured alcohol bath. To this solution was added dropwise 1.5 ml of a solution of 1.6 mol of n-butyllithium/liter of hexane, followed by stirring for 45 minutes. Thereafter, the solution was added to a solution of 2.7 ml of silicon tetrachloride in 10 ml of tetrahydrofuran, and the mixture was stirred at 25° C. for 15 minutes. Further, 100 ml of heptane was added and tetrahydrofuran was distilled off. The heptane layer was removed and dried under vacuum after it was washed with hexane. The product was dissolved in 50 ml of dichloromethane and after lithium chloride which precipitated was removed, the product was dried under vacuum to yield 1.65 g of product (B).

1.65 Grams of product (B) was dissolved in 30 ml of dichloromethane and 0.31 g of dimethylanilinium chloride was added, and the mixture was stirred at 25° C. for 5 minutes. Lithium chloride which precipitated was removed and the product was dried under vacuum to yield 1.7 g of dimethylanilinium 4-trichlorosilyl-2,3,5,6-tetrafluorophenyltris(pentafluorophenyl)borate. Its chemical structure was confirmed by NMR data measured (a part of which is shown below).

$^1$H-NMR (CD$_2$Cl$_2$): δ3.23(6H), 7.50(2H), 7.57(3H), 11.5 (1H);

$^{19}$F-NMR (CD$_2$Cl$_2$): δ−131.0, −131.6, −132.9, −163.4, −167.3

EXAMPLE 2

Production of Dimethylanilinium 4-dimethylchlorosilyl-2,3,5,6-tetrafluorophenyltris(pentafluorophenyl)borate [Ionic Compound]

7.5 Grams (50 mmol) of 1,2,4,5-tetrafluorobenzene was dissolved in 50 ml of diethyl ether and cooled in a dry ice/denatured alcohol bath. To the solution was added dropwise 31.3 ml of a solution of 1.6 mol of n-butyllithium/liter of hexane, followed by stirring for 30 minutes. The resulting solution was added to 883 ml (50 mmol) of 2.9% isoparaffin solution of tris(pentafluorophenyl)borane, and stirred at 25° C. for 30 minutes. Upon this, product (C) precipitated. The solution layer was removed and washed with hexane, followed by drying under vacuum. The product (C) was recrystallized from diethyl ether (yield: 34.5 g).

8.44 Grams (9.5 mmol) of the product (C) was dissolved in 30 ml of tetrahydrofuran and cooled in a dry ice/denatured alcohol bath. To this solution was added dropwise 6.25 ml of a solution of 1.6 mol of n-butyllithium/liter of hexane, followed by stirring for 45 minutes. The resulting solution was added to 50 ml of tetrahydrofuran having dissolved therein 12 ml (10 mmol) of dimethyldichlorosilane, and stirred at 25° C. for 30 minutes. After the stirring, 100 ml of heptane was added and tetrahydrofuran was distilled off. The heptane layer was removed and washed with hexane, followed by drying under vacuum. The product was dissolved in 30 ml of dichloromethane, to which was added 20 ml of a dichloromethane solution of 2.99 g (19.0 mmol) of N,N-dimethylaniline hydrochloride. The solution was stirred for 30 minutes and lithium chloride which precipitated was removed and dried under vacuum to yield 1.6 g of dimethylanilinium 4-dimethylchlorosilyl-2,3,5,6-tetrafluorophenyltris(pentafluorophenyl)borate. Its chemical structure was confirmed by NMR data measured (a part of which is shown below).

$^1$H-NMR (CD$_2$Cl$_2$): δ0.77(6H), 3.23(6H), 7.50(6H), 7.57 (3H), 11.5(1H);

$^{19}$F-NMR (CD$_2$Cl$_2$): δ−128.6, −129.1, −130.0, −159.8, −163.6.

EXAMPLE 3

Production of Dimethylanilinium 4-(8-(dimethylchlorosilyl)-octyldichlorosilyl-2,3,5,6-tetrafluorophenyl-tris(pentafluorophenyl)borate [Ionic Compound]

The same procedures as in Example 2 were repeated except that 1,8-bis(dimethylchlorosilyl)octane was used in place of dimethyldichlorosilane to yield 2.3 g of dimethylanilinium 4-(8-(dimethylchlorosilyl)-octyldichlorosilyl)-2,3,5,6-tetrafluorophenyltris(pentafluorophenyl) borate.

COMPARATIVE EXAMPLE 1

Production of Dimethylanilinium 4-dimethylchlorosilylphenyl-tris(pentafluorophenyl)borate [Ionic Compound]

The same procedures as in Example 2 were repeated except that 1,4-dibromobenzene was used in place of 1,2,4,5-tetrafluorobenzene to yield 0.8 g of the target compound, dimethylanilinium 4-dimethylchlorosilylphenyl-tris(pentafluorophenyl)borate.

EXAMPLE 4

Preparation of Components for Olefin Polymerization Catalyst from the Compound of Example 1

To 30 ml of dichloromethane was added 0.5 g of silica dried at 150° C. and at 0.5 mmHg for 4 hours, with adding 6 ml of a dichloromethane solution containing 56 μmol/ml of the ionic compound having a carrier bondable functional group obtained in Example 1 while stirring, and the resulting solution was refluxed for 2 hours. This was washed three times with 20 ml of dichloromethane at 40° C. and dried under vacuum.

The olefin polymerization catalyst component thus obtained was measured for its boron content by Induction Combined High Frequency Plasma (ICP) spectrophotometry. As a result, it was confirmed that the 0.25 mmol of the ionic compound of Example 1 was carried per g of the catalyst component. After the carrying, the amount of hydroxyl groups on the surface of silica was determined by measuring the amount of ethane which is formed as a result of the reaction between the hydroxyl groups on the surface of silica and triethylaluminum. As a result, the hydroxyl groups of the silica moiety was confirmed to be decreased by about 0.25 mmol/g. From this result, it is understood that substantially all the ionic compounds carried on silica reacted with the hydroxyl groups on the surface of silica. Further, formation of hydrogen chloride upon the reaction between the ionic compounds and silica by contacting the gaseous dichloromethane used in the reaction solvent with water, neutralizing with sodium carbonate and titrating with an aqueous silver nitrate solution using potassium chromate as an indicator.

The olefin polymerization catalyst component thus obtained was washed three times with boiling dichloromethane. There was observed almost no change in the amount of the ionic compound carried, which confirmed that the ionic compound and the carrier bonded to each other with sufficient strength.

EXAMPLE 5

Preparation of Components for Olefin Polymerization Catalyst from the Compound of Example 2

An olefin polymerization catalyst component was prepared in the same manner as in Example 4 except that the compound of Example 2 was used as the ionic compound having a carrier bondable functional group. The amount of the ionic compound carried was 0.27 (mmol of ionic compound/g of catalyst component).

EXAMPLE 6

Preparation of Components for Olefin Polymerization Catalyst from the Compound of Example 3

An olefin polymerization catalyst component was prepared in the same manner as in Example 4 except that the compound of Example 3 was used as the ionic compound having a carrier bondable functional group. The amount of the ionic compound carried was 0.23 (mmol of ionic compound/g of catalyst component).

COMPARATIVE EXAMPLE 2

Preparation of Components for Olefin Polymerization Catalyst from the Compound of Comparative Example 1

An olefin polymerization catalyst component was prepared in the same manner as in Example 4 except that the compound of Comparative Example 1 was used as the ionic compound having a carrier bondable functional group. The amount of the ionic compound carried was 0.17 (mmol of ionic compound/g of catalyst component).

COMPARATIVE EXAMPLE 3

Preparation of Comparative Olefin Polymerization Catalyst Component

A comparative olefin polymerization catalyst component was prepared in the same manner as in Example 4 except that N,N-dimethylanilinium tetrakis(pentafluorophenyl)borate was used in place of the ionic compound having a carrier bondable functional group. The amount of the ionic compound carried was less than 0.005 (mmol of ionic compound/g of catalyst component).

EXAMPLE 7

Preparation of an Olefin Polymerization Catalyst from the Catalyst Component of Example 4 and Olefin Polymerization

[Preparation of Catalyst]

4 ml of a solution containing 0.5 mmol of rac-ethylene-bisindenylzirconium dichloride (hereafter, abbreviated as "EBIZ")/liter of toluene was contacted with 0.2 ml of a solution of 0.5 mol of triisobutylaluminum/liter of toluene, to which was added 30 mg of the olefin polymerization catalyst component of Example 4. After stirring the solution for 2 minutes, toluene was removed and 5.0 ml of hexane was added to form a hexane slurry.

[Polymerization of Propylene]

In a 1.5 liter autoclave were charged 6 ml of a hexane solution of 0.5 mol of triisobutylaluminum/liter of hexane and 8 mol of propylene. After elevating the temperature to 50° C., the above-described slurry type olefin polymerization catalyst was added and polymerization was continued for 60 minutes. The polymerization activity was 85,000 g/g of complex/h, and 2,000 g/g of catalyst/h. Table 1 shows the results obtained. The bulk density of the resulting polymer was as high as 0.40 g/ml, showing no attachment to the wall of the reactor.

EXAMPLE 8

Preparation of an Olefin Polymerization Catalyst from the Catalyst Component of Example 5 and Olefin Polymerization

[Preparation of Catalyst]

30 mg of the olefin polymerization catalyst component of Example 5 was contacted with 1.0 ml of a solution containing 0.5 mol of triisobutylaluminum/liter of toluene, to which was added 4.0 ml of a solution containing 0.5 mol of EBIZ/liter of toluene. After stirring the solution for 3 minutes, toluene was removed and 5.0 ml of hexane was added to form a hexane slurry.

[Polymerization of Propylene]

The procedures of Example 7 were repeated except that the above-described olefin polymerization catalyst was used. As a result, granular polymer was obtained. Table 1 shows the results.

[Copolymerization of Propylene with Ethylene]

In a 5 liter autoclave were charged 6 ml of a hexane solution of 0.5 mol of triisobutylaluminum/liter of hexane and 8 mol of propylene. After elevating the temperature to 50° C., the pressure was raised so that the partial pressure of ethylene reached 1 kg/cm$^2$, and the above-described olefin polymerization catalyst was added and polymerization was continued for 30 minutes. Table 2 shows the results. The polymerization activity was 130,000 g/g of complex/h/atm, and 10,000 g/g of catalyst/h. The resulting polymer was granular and had a bulk density as high as 0.35 g/ml, showing no attachment to the wall of the reactor.

[Polymerization of Ethylene]

In a 1.5 liter autoclave were charged 8 ml of a toluene solution of 0.5 mol of triisobutylaluminum/liter of toluene, 100 mg of the olefin polymerization catalyst, and 700 ml of isobutane. After elevating the temperature to 70° C., the pressure was raised so that the partial pressure of ethylene reached 10 kg/cm$^2$, and polymerization was continued for 30 minutes. The polymerization activity was 150,000 g/g of complex/h/atm, and 1,000 g/g of catalyst/h/atm. Table 3 shows the results. The resulting polymer had a bulk density as high as 0.35 g/ml, showing no attachment to the wall of the reactor.

EXAMPLE 9

Preparation of an Olefin Polymerization Catalyst from the Catalyst Component of Example 4 and Olefin Polymerization

[Preparation of Catalyst]

An olefin polymerization catalyst was prepared in the same manner as in Example 8 except that removal of the supernatant, washing with toluene, and slurry formation with hexane were not carried out.

[Polymerization of Propylene]

In a 1.5 liter autoclave were charged 1.0 ml of a hexane solution of 0.1 mol of n-butyllithium/liter of hexane and 8 mol of propylene. After elevating the temperature to 50° C., the above-described olefin polymerization catalyst was added and polymerization was continued for 60 minutes. Table 1 shows the results. The polymer was granular and showed no attachment to the wall of the reactor.

[Copolymerization of Propylene with Ethylene]

In a 1.5 liter autoclave were charged 1.0 ml of a hexane solution of 0.1 mol of n-butyllithium/liter of hexane and 8 mol of propylene. After elevating the temperature to 50° C., the pressure was raised so that the partial pressure of ethylene reached 1.0 kg/cm$^2$, and the above-described olefin polymerization catalyst was added and polymerization was continued for 30 minutes. Table 2 shows the results. The resulting polymer was granular and showed no attachment to the wall of the reactor.

[Polymerization of Ethylene]

In a 1.5 liter autoclave were charged 1.0 ml of a hexane solution of 0.1 mol of n-butyllithium/liter of hexane and 700 ml of isobutane. After elevating the temperature to 70° C., the pressure was raised so that the partial pressure of ethylene reached 10.0 kg/cm$^2$, and polymerization was continued for 60 minutes. Table 3 shows the results. The resulting polymer was granular and showed no attachment to the wall of the reactor.

EXAMPLE 10

Preparation of an Olefin Polymerization Catalyst from the Catalyst Component of Example 5 and Olefin Polymerization

[Preparation of Catalyst]

An olefin polymerization catalyst was prepared in the same manner as in Example 8 except that the olefin polymerization catalyst component of Example 5 was used.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

EXAMPLE 11

Preparation of an Olefin Polymerization Catalyst from the Catalyst Component of Example 6 and Olefin Polymerization

[Preparation of Catalyst]

An olefin polymerization catalyst was prepared in the same manner as in Example 8 except that the olefin polymerization catalyst component of Example 6 was used.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

EXAMPLE 12

Preparation of an Olefin Polymerization Catalyst from the Catalyst Component of Example 4 and Olefin Polymerization

[Preparation of Catalyst]

An olefin polymerization catalyst was prepared in the same manner as in Example 8 except that rac-isopropylidene(3-t-butylcyclopentadienyl){1-(3-t-butylindenyl)}zirconium dichloride (hereafter, abbreviated as "CTITZ") was used instead of EBIZ.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

EXAMPLE 13

Preparation of an Olefin Polymerization Catalyst from the Catalyst Component of Example 4 and Olefin Polymerization

[Preparation of Catalyst]

An olefin polymerization catalyst was prepared in the same manner as in Example 8 except that rac-dimethylsilylenebis{1-(2-methyl-4-benzoindenyl)}zirconium dichloride (hereafter, abbreviated as "2MBIZ") was used instead of EBIZ.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

EXAMPLE 14

Preparation of an Olefin Polymerization Catalyst from the Catalyst Component of Example 4 and Olefin Polymerization

[Preparation of Catalyst]

An olefin polymerization catalyst was prepared in the same manner as in Example 8 except that rac-dimethylsilylenebis{1-(2-methyl-4-phenylindenyl)}zirconium dichloride (hereafter, abbreviated as "2MPIZ") was used instead of EBIZ.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

EXAMPLE 15

Preparation of an Olefin Polymerization Catalyst from the Catalyst Component of Example 4 and Olefin Polymerization

[Preparation of Catalyst]

An olefin polymerization catalyst was prepared in the same manner as in Example 8 except that rac-dimethylsilylenebis{1-(2-methyl-4-naphthylindenyl)}zirconium dichloride (hereafter, abbreviated as "2MNIZ") was used instead of EBIZ.

[Polymerization of Propylene]

The propylene polymerization procedures of Example 8 were repeated except that the above-described olefin polymerization catalyst was used to yield a granular polymer. Table 1 shows the results.

[Copolymerization of Propylene and Ethylene]

The procedures of copolymerization of propylene and ethylene described in Example 8 were repeated except that the above-described olefin polymerization catalyst was used to yield a granular polymer. Table 2 shows the results.

[Polymerization of Ethylene]

The ethylene polymerization procedures of Example 8 were repeated except that the above-described olefin polymerization catalyst was used to yield a granular polymer. Table 3 shows the results.

COMPARATIVE EXAMPLE 4

Preparation of an Olefin Polymerization Catalyst from the Catalyst Component of Comparative Example 3 and Olefin Polymerization

[Preparation of Catalyst]

An olefin polymerization catalyst was prepared in the same manner as in Example 8 except that the olefin polymerization catalyst component of Comparative Example 3 was used.

[Polymerization of Propylene]

The propylene polymerization procedures of Example 8 were repeated except that the above-described olefin polymerization catalyst was used. Table 1 shows the results. Almost no polymerization activity was observed.

[Copolymerization of Propylene and Ethylene]

The procedures of copolymerization of propylene and ethylene described in Example 8 were repeated except that the above-described olefin polymerization catalyst was used. Table 2 shows the results. Almost no polymerization activity was observed.

[Polymerization of Ethylene]

The ethylene polymerization procedures of Example 8 were repeated except that the above-described olefin polymerization catalyst was used. Table 3 shows the results. Almost no polymerization activity was observed.

COMPARATIVE EXAMPLE 5

Preparation of Comparative Olefin Polymerization Catalyst and Olefin Polymerization

[Preparation of Catalyst]

4 ml of a solution of 0.5 mmol of EBIZ/liter of toluene was contacted with 0.2 ml of a solution of 0.5 mol of triisobutylaluminum/liter of toluene, to which was added 2 ml of a solution of 1 mmol of N,N-dimethylanilinium tetrakis(pentafluorophenyl)borate/liter of toluene. After stirring for 2 minutes, 30 mol of toluene and 0.5 g of silica (dried at 450° C. for 4 hours) were added. After stirring the solution for 5 minutes, toluene was removed and the residue was washed with hexane and converted into a hexane slurry.

[Polymerization of Propylene]

In a 1.5 liter autoclave were charged 6 ml of a hexane solution of 0.5 mol of triisobutylaluminum/liter of hexane and 8 mol of propylene. After elevating the temperature to 50° C., the above-described olefin polymerization catalyst was added and polymerization was continued for 30 minutes. The polymerization activity was 7,400 g/g of complex/h, and 130 g/g of catalyst/h. Table 1 shows the results obtained. The resulting polymer had a bulk density as high as 0.12 g/ml and was fine powder showing attachment to the wall of the reactor to some extent.

[Copolymerization of Propylene and Ethylene]

The procedures of copolymerization of propylene and ethylene described in Example 8 were repeated except that the above-described olefin polymerization catalyst was used. Table 2 shows the results. The resulting polymer was fine powder showing attachment to the wall of the reactor to some extent.

[Polymerization of Ethylene]

The ethylene polymerization procedures of Example 8 were repeated except that the above-described olefin polymerization catalyst was used. Table 3 shows the results.

COMPARATIVE EXAMPLE 6

Preparation of an Olefin Polymerization Catalyst from the Catalyst Component of Comparative Example 2 and Olefin Polymerization

[Preparation of Catalyst]

An olefin polymerization catalyst was prepared in the same manner as in Example 8 except that the olefin polymerization catalyst component of Comparative Example 2 was used.

[Polymerization of Propylene]

The propylene polymerization procedures of Example 8 were repeated except that the above-described olefin polymerization catalyst was used. A granular polymer was obtained. Table 1 shows the results.

[Copolymerization of Propylene and Ethylene]

The procedures of copolymerization of propylene and ethylene described in Example 8 were repeated except that the above-described olefin polymerization catalyst was used. A granular polymer was obtained. Table 2 shows the results.

[Polymerization of Ethylene]

The ethylene polymerization procedures of Example 8 were repeated except that the above-described olefin polymerization catalyst was used. Table 3 shows the results.

TABLE 1

Polymerization of Propylene

| Example | Activity of Polymerization gPP/complex/h | gPP/Catalyst/h | Density g/ml | Attachment of Polymer |
|---|---|---|---|---|
| 7 | 85,000 | 2,000 | 0.40 | No |
| 8 | 30,000 | 600 | 0.41 | No |
| 9 | 66,000 | 1,700 | 0.40 | No |
| 10 | 100,000 | 7,000 | 0.43 | No |
| 11 | 62,000 | 3,300 | 0.39 | No |
| 12 | 55,000 | 3,000 | 0.40 | No |
| 13 | 31,000 | 1,700 | 0.40 | No |
| 14 | 20,000 | 1,500 | 0.35 | No |
| 15 | 40,000 | 2,000 | 0.40 | No |
| C. Ex. 4 | 0 | 0 | — | — |
| C. Ex. 5 | 7,400 | 130 | 0.12 | Yes |
| C. Ex. 6 | 5,000 | 300 | 0.37 | No |

TABLE 2

Copolymerization of Propylene and Ethylene

| Example | Activity of Polymerization gPP/mmol Complex/h | gPP/g Catalyst/h | Density g/ml | Attachment of Polymer |
|---|---|---|---|---|
| 8 | 130,000 | 10,000 | 0.35 | No |
| 9 | 260,000 | 11,000 | 0.35 | No |
| 10 | 320,000 | 29,000 | 0.35 | No |
| 11 | 160,000 | 10,000 | 0.37 | No |
| 12 | 380,000 | 6,300 | 0.32 | No |
| 13 | 230,000 | 13,000 | 0.33 | No |
| 14 | 310,000 | 21,000 | 0.30 | No |
| 15 | 100,000 | 7,000 | 0.39 | No |
| C. Ex. 4 | 0 | 0 | — | — |
| C. Ex. 5 | 30,000 | 3,000 | 0.13 | Yes |
| C. Ex. 6 | 20,000 | 2,000 | 0.35 | No |

TABLE 3

Polymerization of Ethylene

| Example | Activity of Polymerization gPE/mmol Complex/h/atm | gPE/g Catalyst/h/atm | Density g/ml | Attachment of Polymer |
|---|---|---|---|---|
| 8 | 150,000 | 1,000 | 0.35 | No |
| 9 | 100,000 | 2,000 | 0.32 | No |
| 10 | 70,000 | 1,200 | 0.32 | No |
| 11 | 75,000 | 1,500 | 0.35 | No |
| 12 | 70,000 | 600 | 0.31 | No |
| 13 | 70,000 | 1,000 | 0.31 | No |
| 14 | 11,000 | 1,300 | 0.34 | No |
| 15 | 60,000 | 550 | 0.35 | No |
| C. Ex. 4 | 0 | 0 | — | — |
| C. Ex. 5 | 80,000 | 200 | 0.15 | Yes |
| C. Ex. 6 | 8,000 | 140 | 0.33 | No |

INDUSTRIAL APPLICABILITY

The ionic compound of this invention, which is used in combination with a carrier, an organometal compound and a Group 4, 5 or 6 transient metal compound, is useful as a catalyst component for olefin polymerization by a slurry process, gas phase process or the like. Using the ionic compound of this invention, catalysts having excellent bonding ability with the carrier can be obtained and it is possible therewith to produce polyolefins having improved powder characteristics and showing no attachment to the inner wall of a reactor.

The catalyst of this invention is useful for producing a wide variety of polymers from monomers such as ethylene, propylene, 1-butene, 3-methyl-1-butene, 1-hexene, 4-methyl-1-pentene, 1-octene, 1-decene, 1-dodecene, 1-tetradecene, 1-hexadecene, 1-octadecene, 1-eicosene, cyclopentene, cycloheptene, norbornene, 5-methyl-2-norbornene, tetracyclododecene, and further styrene, vinylcyclohexane, vinylcyclohexene, divinylbenzene, dienes, etc.

We claim:

1. Ionic compounds represented by general formula (I) below:

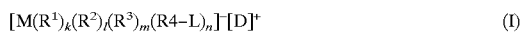

$$[M(R^1)_k(R^2)_l(R^3)_m(R^4-L)_n]^-[D]^+ \qquad (I)$$

wherein, M is an element belonging to Group 13;

$R^1$, $R^2$ and $R^3$, which may be the same or different, each represent a $C_1$–$C_{20}$ hydrocarbyl group, a substituted hydrocarbyl group, an alkoxide group, or a halogen atom;

$R^4$ represents a $C_1$–$C_{20}$ alkylene group, a substituted alkylene group, a substituted phenylene group, a silanylene group, a substituted silanylene group, a silalkylene group, a substituted silalkylene group, an oxasilanylene group, a substituted oxasilanylene group, or an oxasilalkylene group, with k, l and m each being 0 or an integer of 1 to 3, and n being an integer of 1 to 4 such that k+l+m+n=4;

L is a group represented by general formula (II) or (III) below and is chemically bonded to $R^4$:

$$SiR^5R^6R^7 \qquad (II)$$

$$R^8R^9R^{10}SiYSiR^{11}R^{12} \qquad (III)$$

wherein $R^5$ to $R^{12}$, which may be the same or different, each represent a $C_1$–$C_{20}$ hydrocarbyl group, a substituted hydrocarbyl group, an alkoxide group, or a halogen atom, with at least one of $R^5$, $R^6$ and $R^7$ and at least one of $R^8$, $R^9$ and $R^{10}$ being a halogen atom;

Y is —O—, a $C_1$–$C_{20}$ alkylene group, a substituted alkylene group, a phenylene group, a substituted phenylene group, or a group represented by formula:

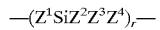
$$-(Z^1SiZ^2Z^3Z^4)_r-$$

wherein $Z^1$ and $Z^4$, which may be the same or different, each represent an alkylene group, a substituted alkylene group, a phenylene group, a substituted phenylene group, —O—, an oxyalkylene group, a substituted oxyalkylene group, an oxyphenylene group, or a substituted oxyphenylene group; $Z^2$ and $Z^3$, which may be the same or different, each represent a hydrogen atom, an alkyl group, a substituted alkyl group, a phenyl group, or a substituted phenyl group; r is an integer of at least 1;

when n is 2 or more, each $R^4$–L may be the same or different;

D is a monovalent cation selected from the group consisting of carbonium, anilinium, ammonium, ferrocenium, phosphonium, sodium, potassium, or lithium.

2. The ionic compound as claimed in claim 1, wherein n is 1.

3. The ionic compound as claimed in claim 1, wherein M is boron.

4. The ionic compound as claimed in claim 1, wherein $R^1$, $R^2$ and $R^3$ are each a pentafluorophenyl group.

5. The ionic compound as claimed in claim 1, wherein L is a halogenated silyl group, a halogenated substituted silyl group, a halogenated silalkyl group, a halogenated substituted silalkyl group, a halogenated oxasilyl group, a halogenated substituted oxasilyl group, or a halogenated oxasilalkyl group.

6. The ionic compound as claimed in claim 1, wherein $R^4$ is a substituted phenylene group.

7. The ionic compound as claimed in claim 6, wherein $R^4$ is a 2,3,5,6-tetrafluorophenylene group.

8. The ionic compound as claimed in claim 1, wherein L is a trichlorosilyl group, a methyldichlorosilyl group, or a dimethylchlorosilyl group.

9. The ionic compound as claimed in claim 1, wherein D is an anilinium ion.

10. A method of producing ionic compounds represented by general formula (I)

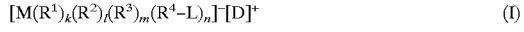
$$[M(R^1)_k(R^2)_l(R^3)_m(R^4-L)_n]^-[D]^+ \qquad (I)$$

wherein M, $R^1$, $R^2$, $R^3$, $R^4$, L, D, k, l, m, and n in the formula have the same meanings as in claim 1, comprising the steps of: reacting components represented by (1) to (4) below:

(1) a compound represented by general formula (IV):

$$X^1-R^4-X^2 \qquad (IV)$$

wherein $X^1$ and $X^2$ independently represent a hydrogen atom or a bromine atom, and $R^4$ has the same meaning as in claim 1;

(2) a compound represented by general formula (V):

$$MR^1R^2R^3 \qquad (V)$$

wherein M is an element belonging to Group 13; and $R^1$, $R^2$ and $R^3$, which may be the same or different, each represent a $C_1$–$C_{20}$ hydrocarbyl group, a substituted hydrocarbyl group, an alkoxide group or a halogen atom;

(3) a compound represented by general formula (VI) or (VII):

$$SiR^5R^6R^7R^{13} \qquad (VI)$$

$$R^8R^9R^{10}SiYSiR^{11}R^{12}R^{14} \qquad (VII)$$

wherein $R^5$ to $R^{14}$, which may be the same or different, each represent a $C_1$–$C_{20}$ hydrocarbyl group, a substituted hydrocarbyl group, an alkoxide group, or a halogen atom; and (4) a halide of a monovalent cation.

11. A method of producing ionic compounds represented by general formula (I)

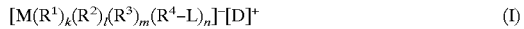
$$[M(R^1)_k(R^2)_l(R^3)_m(R^4-L)_n]^-[D]^+ \qquad (I)$$

wherein M, $R^1$, $R^2$, $R^3$, $R^4$, L, D, k, l, m, and n in the formula have the same meanings as in claim 1, comprising the steps of:

(a) substituting bromine or hydrogen of a compound represented by general formula (IV)

$$X^1-R^4-X^2 \qquad (IV)$$

wherein $X^1$ and $X^2$ independently represent a hydrogen atom or a bromine atom, and $R^4$ represents a $C_1$–$C_{20}$ alkylene group, a substituted alkylene group, a substituted phenylene group, a silanylene group, a substituted silanylene group, a silalkylene group, a substituted silalkylene group, an oxasilanylene group, a substituted oxasilanylene group, or an oxasilalkylene group, with lithium of an organic lithium to obtain a lithium substituted compound;

(b) reacting the lithium substituted compound with a Group 13 element-containing compound represented by general formula (V)

$$MR^1R^2R^3 \qquad\qquad (V)$$

wherein $R^1$, $R^2$ and $R^3$, which may be the same or different, each represent a $C_1$–$C_{20}$ hydrocarbyl group, a substituted hydrocarbyl group, an alkoxide group or a halogen atom, to obtain a lithium compound represented by formula (VIII)

$$[M(R^1)_k(R^2)_l(R^3)_m(R^4-A)_n]^-[Li]^+ \qquad\qquad (VIII)$$

wherein A is hydrogen or bromine chemically bonded to $R^4$;

(c) lithionating the compound of general formula (VIII) with an organic lithium and then reacting with a silicon compound represented by general formula (VI) or (VII) below $$SiR^5R^6R^7R^{13} \qquad\qquad (VI)$$

$$R^8R^9R^{10}SiYSiR^{11}R^{12}R^{14} \qquad\qquad (VII)$$

wherein $R^5$ to $R^{14}$, which may be the same or different, each represent a $C_1$–$C_{20}$ hydrocarbyl group, a substituted hydrocarbyl group, an alkoxide group, or a halogen atom, to obtain a compound represented by general formula (IX)

$$[M(R^1)_k(R^2)_l(R^3)_m(R^4-L)_n]^-[Li]^+ \qquad\qquad (IX); and$$

(d) reacting the compound of general formula (IX) with a halide of a monovalent cation.

12. The method of producing the ionic compounds as [described] claimed in claim 10 or 11, wherein the compound of general formula (IV) is a compound represented by general formula (IVa)

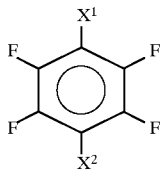

(IVa)

wherein $X^1$ and $X^2$ independently represent a hydrogen atom or a bromine atom.

13. A catalyst component for olefin polymerization comprising the ionic compound as claimed in claim 1 chemically bonded to a carrier.

14. The catalyst component as claimed in claim 13, wherein the carrier is a solid having a functional group represented by general formula (X)

$$—OR \qquad\qquad (X)$$

wherein R is a hydrogen atom, a $C_1$–$C_{20}$ alkyl group, alkali metal or amine.

15. The catalyst component as claimed in claim 14, wherein the carrier is a solid having a hydroxyl group.

16. The catalyst component as claimed in claim 13, wherein the carrier is silica, alumina or mixtures thereof.

17. A catalyst for olefin polymerization comprising the following as essential components:

(a) the catalyst component for olefin polymerization as claimed in claim 13, (b) an organometallic compound, and (c) a Group 4, 5 or 6 transtion metal compound.

18. The catalyst as claimed in claim 17, wherein the Group 4, 5 or 6 transition metal compound is a metallocene.

* * * * *